(12) United States Patent  (10) Patent No.: US 8,568,325 B2
Moritz  (45) Date of Patent: Oct. 29, 2013

(54) METHOD AND APPARATUS FOR CONTROLLING POWER OF AN ULTRASOUND SYSTEM

(75) Inventor: Michael R. Moritz, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 2519 days.

(21) Appl. No.: 11/157,100

(22) Filed: Jun. 20, 2005

(65) Prior Publication Data

US 2007/0016021 A1 Jan. 18, 2007

(51) Int. Cl.
*A61B 8/00* (2006.01)

(52) U.S. Cl.
USPC .................. 600/447; 600/407; 600/437

(58) Field of Classification Search
USPC .................. 600/474, 443–447; 601/2
See application file for complete search history.

(56) References Cited

U.S. PATENT DOCUMENTS

| 5,181,514 | A | * | 1/1993 | Solomon et al. ............. 600/444 |
| 5,482,046 | A |   | 1/1996 | Deitrich |
| 6,312,381 | B1 | * | 11/2001 | Knell et al. .................. 600/437 |
| 6,471,651 | B1 | * | 10/2002 | Hwang et al. ................ 600/459 |
| 6,542,846 | B1 | * | 4/2003 | Miller et al. ................ 702/132 |
| 6,592,521 | B1 |   | 7/2003 | Urbano et al. |
| 6,652,463 | B2 | * | 11/2003 | Hunt et al. .................. 600/458 |
| 2004/0267119 | A1 |   | 12/2004 | Adams |
| 2005/0228284 | A1 |   | 10/2005 | Baumgartner et al. |
| 2006/0074320 | A1 |   | 4/2006 | Yoo et al. |
| 2006/0092930 | A1 | * | 5/2006 | Shah .......................... 370/389 |

* cited by examiner

*Primary Examiner* — Unsu Jung
*Assistant Examiner* — Saurel J Selkin
(74) *Attorney, Agent, or Firm* — The Small Patent Law Group; Dean D. Small

(57) ABSTRACT

A medical imaging system with a scanning subsystem configured to acquire imaging data is provided. Also provided is a controller configured to selectively control power to at least one component of the system based on a mode of operation of the scanning subsystem.

19 Claims, 3 Drawing Sheets

METHOD AND APPARATUS FOR CONTROLLING POWER OF AN ULTRASOUND SYSTEM

BACKGROUND OF THE INVENTION

The invention relates generally to diagnostic imaging systems, and more particularly, to power management of diagnostic imaging systems.

At least some known ultrasound diagnostic imaging systems maintain power to the image data acquisition circuitry even when the circuitry is not actively performing a scan of a patient. Thus, image data acquisition circuitry consumes power even when imaging data is not being acquired.

A front end of the ultrasound system, also known as a scanning portion or scanning sub-system, generally includes a scanning probe, transmit circuitry for transmitting an ultrasound pulse into a patient, and image acquisition circuitry for collecting echo information from the back scattered echoes of the transmitted ultrasound pulse. The front end is typically includes customized circuits, such as, for example, application specific integrated circuits (ASICs) that perform transmit and receive functions related to image data acquisition. A back end of the ultrasound system typically includes a back end processor (BEP) or controller, for example, a personal computer (PC) or other processor. Although some final image processing may be performed by the BEP, the BEP may be used to perform functions not involving active scanning of the patient. The functions not involved in active scanning include, for example, setup of the ultrasound system for various types of scans, generating patient reports, reviewing the scanned data and/or generated images, etc. Typically, power is supplied to and consumed by the front end of an ultrasound system even when the front end is not actively scanning the patient.

Power is typically consumed by the front end and back end circuitry of an ultrasound system regardless of a mode of operation of the system. For example, a user or sonographer may not be actively performing scanning of the patient when generating patient reports or analyzing acquired images. This unnecessary power consumption by the front end circuitry during non-scanning periods may lead to unnecessary generation of heat, which may decrease reliability of the system. Fans may operate to dissipate the heat produced by consumption of power by the front end circuitry, which also leads to added cost.

A trend in medical ultrasound systems is to process a larger number of channels (e.g. transducer elements) and multiple lines of acquisition (MLA) of data, which tends to increase the power consumption within the transmit and receiver sections of the front end. Increased power consumption leads to increased heat generation and decreased reliability due to the heat.

Thus, in these known ultrasound systems, power is supplied to and consumed by various portions of the ultrasound system when scanning is not active. This power consumption results in unnecessary heat generation and decrease in system reliability.

BRIEF DESCRIPTION OF THE INVENTION

In one embodiment, a medical imaging system is provided. A scanning subsystem of the medical imaging system is configured to acquire imaging data. A controller is configured to selectively control power consumption to at least one component of the system based on a mode of operation of the scanning subsystem.

In another embodiment, a medical imaging system is provided with image acquisition circuits and image processing circuits. The image acquisition circuits are configured to acquire imaging data. The image processing circuits are configured to process the acquired imaging data. A controller is configured to selectively control power consumption by at least one of the image acquisition circuits.

In yet another embodiment, a method for controlling power of a medical imaging system is provided. The method determines a mode of operation of the medical imaging system. The method identifies circuit components to control power to based on the mode of operation. The method then controls a power level supplied to the at least one of said identified circuit components based on the mode of operation.

In another embodiment, a method for managing power consumption by a medical imaging system is provided. The method determines a mode of operation of the system. The method identifies circuit components to power manage based on the mode of operation of the system. The method then controls power consumed by at least one of said identified circuit components.

DETAILED DESCRIPTION OF THE INVENTION

Figure 1:
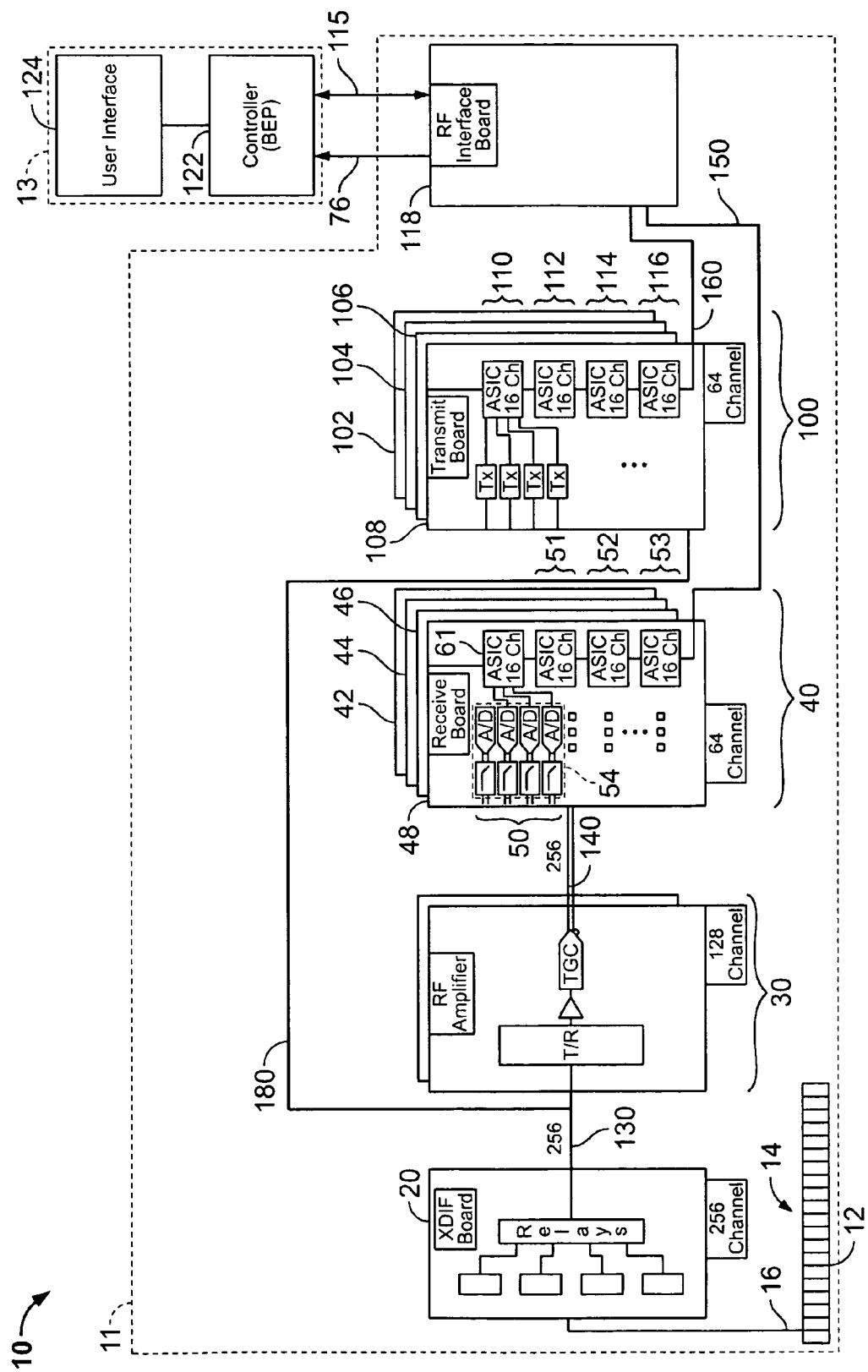
FIG. 1 is a block diagram of an ultrasound system constructed in accordance with an embodiment of the present invention.

FIG. 1 is a block diagram of an ultrasound medical imaging system 10 constructed in accordance with an embodiment of the present invention. The ultrasound system 10 includes a scanning subsystem 11, also known as a front end processor 11, and a back end processor 13. The scanning subsystem 11 includes a transducer array 14, that may be configured as a probe, having transducer elements 12, a transducer interface board 20, preamplifier boards group 30, receiver boards group 40, transmit boards group 100, and a Radio Frequency Interface (RFI) board 118. The back end processor 13 includes a controller 122, also known as a back end processor (BEP) 122, and a user interface 124.

Each receiver board 42, 44, 46, and 48 of the receiver boards group 40 has a similar architecture of receiver circuits, and thus, only one receiver board 48 will be described, with the other receiver boards having similar structure. The receiver board 48 includes a plurality of Application Specific Integrated Circuit (ASIC) component groups, namely an ASIC group 50, an ASIC group 51, an ASIC group 52, and an ASIC group 53. Each of the ASIC component groups has a similar architecture, and thus, only one ASIC group 50 will be described. The receiver circuits of ASIC group 50 include an A/D converter group 54 and an ASIC 61, with the A/D converter group 54 providing digital inputs to the ASIC 61.

Each of a plurality of transmit boards 102, 104, 106, and 108 of the transmit boards group 100 has a similar architecture of transmit circuits, and thus, only one of the transmit boards will be described. The transmit board 108 includes a plurality of ASIC component groups, namely an ASIC group 110, an ASIC group 112, an ASIC group 114, and an ASIC group 116. Each of the ASIC component groups has a similar architecture comprised of transmit circuits.

In operation, the RFI board 118 receives commands from the BEP 122 via a control bus 115. The commands define a configuration of an ultrasound pulse or transmit beam to be emitted by the probe 14 into, for example, a patient. The RFI board 118 generates transmit parameters from the received commands and that determine a transmit beam of a certain shape and size from a certain point or points at the surface of the probe 14. The transmit parameters are communicated over a control bus 160 from the RFI board 118 to the transmit boards group 100. The transmit boards group 100 generates transmit signals from the received transmit parameters.

The transmit signals are provided at certain levels and are phased with respect to each other to steer and focus a transmit beam into one or more transmit pulses or firings from the probe 14 as is known. Each of the four ASIC groups 110, 112, 114, and 116 of the transmit board 108 may control, for example, a group of sixteen channels to communicate transmit signals over 64 (4×16) channels of the probe 14. The 64 channels may correspond to 64 of the transducer elements 12 of the probe 14. Likewise, four ASIC groups on each of the transmit boards 102, 104, and 106 may each control a group of sixteen channels to communicate transmit signals to the probe 14. In total, the transmit boards 102, 104, 106, and 108 may control 256 (4×16) channels of transmit signals to the transducer elements 12 of the probe 14. Thus, 256 transducer elements 12 of the probe 14 may be driven and controlled.

The transmit boards group 100 communicates the transmit signals via a connection 180 (e.g., communication link) through the transducer interface board 20 to drive the plurality of transducer elements 12 within the probe 14. The connection 180 contains a plurality of individual channels or communication lines that may correspond to the number of transducer elements 12. The transmit signals excite the transducer elements 12 to emit ultrasound pulses. The ultrasound pulses are phased to form a focused beam along a desired scan line. Ultrasound echoes, which are backscattered ultrasound waves from, for example, tissue and blood samples within the scanned structure, are received at the transducer elements 12 at different times depending on the distance into the tissue from which the signals are back scattered, and the angle at which the signals contact the surface of the probe 14. The probe 14 may be a two-way transducer that converts the backscattered waves (ultrasound echoes) of energy into received signals.

The received signals are communicated in separate channels from the probe 14 over a connection 16 (e.g., communication link) to the transducer interface board 20, which communicates the received signals over a connection 130 to the preamplifier boards group 30. The preamplifier boards group 30 performs time gain compensation (TGC), for example, swept gain, to increase the amplitude of the received signals from increasing depths in the body to compensate for the progressive attenuation of the deeper echoes. The amplified received signals from the preamplifier boards group 30 are communicated over a connection 140 to the receiver boards group 40. In the illustrated example, the connections 16, 130, and 140, each include 256 channels and the channels in the connection 140 are divided into four groups of 64 channels. Each of the four receiver boards 42, 44, 46, and 48 in the receiver boards group 40 receives a group of 64 channels from the preamplifier boards group 30.

The group of 64 channels received at receiver board 48 is subdivided into four groups of sixteen channels in the illustrated example. Each group of sixteen channels is processed by one of the ASIC groups 50, 51, 52, and 53. For example, a group of sixteen channels is received by the A/D converter group 54 of ASIC group 50. The A/D converter group 54 converts the analog signals of the sixteen received channels into sixteen digital signals that are provided as inputs to the ASIC 61. The ASIC 61 of the ASIC group 50 processes the received sixteen digital signals into beam data and may sum and/or combine the beam data with beam data received from a another ASIC group, for example, an ASIC group from a previous receiver board 46. The ASIC group 50 communicates the resulting beam data to a next ASIC group 51 to be summed and/or combined with the beam data processed from the sixteen input signals received at ASIC group 51. In this manner, resulting beam data is communicated from one ASIC group to another ASIC group (e.g., from ASIC group 50 to group 51 to group 52 to group 53), and from receiver board to receiver board (e.g., from receiver board 42 to board 44 to board 46 to board 48), until all signals received from the preamplifier boards group 30 have been processed by the receiver boards group 40 into beam data. The resulting processed beam data from the receiver boards group 40 is communicated to the RFI board 118 via the data bus 150. The RFI board 118 may further process the received beam data and communicate the resulting processed image information to the BEP 122 over a data bus 76. The BEP 122 may then produce and display ultrasound images for display on a display from the received image information for display on a display at the user interface 124. Any known method for processing the acquired scan data to produce an image for display may be used.

Figure 2:
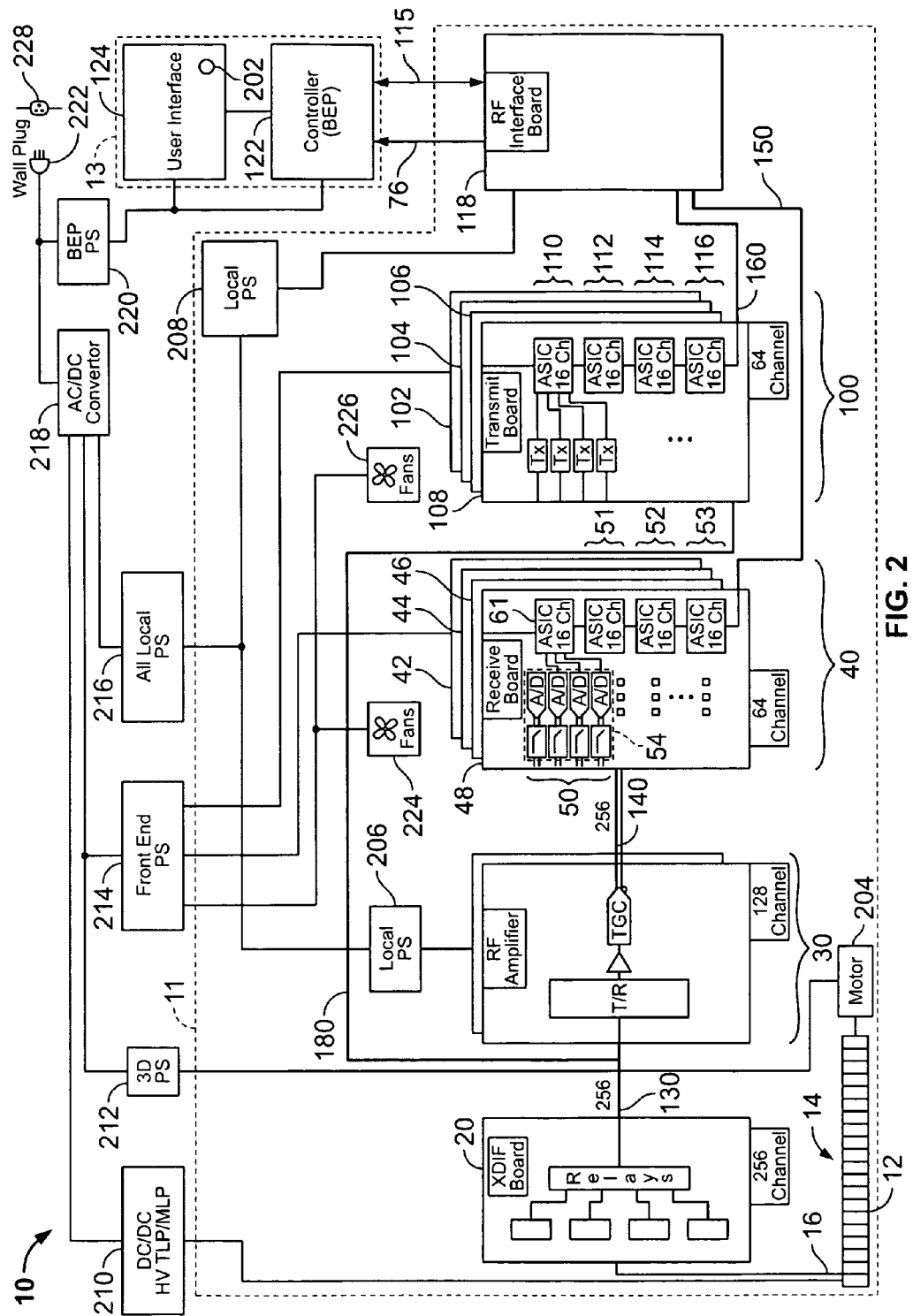
FIG. 2 is a block diagram of the ultrasound system of FIG. 1 showing a plurality of power supplies (PSs).

FIG. 2 is a block diagram of the ultrasound system 10 of FIG. 1 with a plurality power supplies/sources (PSs). A connector, for example, a wall plug 222 receives power from a power source, such as a building wall outlet 228, to provide initial power to the system 10. The power from the plug 222 powers a BEP PS 220 and an AC/DC converter 218. The BEP PS 220 supplies the appropriate voltage for use by the BEP 122 and user interface 124, including, for example, the back end processor 13. The AC/DC converter 218 converts alternating current (AC) power from the wall plug 222 to direct current (DC) power at various voltage levels for use by the system 10 as is known.

The AC/DC converter 218 may supply a DC voltage level of, for example, 48 volts (48V) at a power of 300 watts (W) or 150W to a DC/DC High Voltage (HV) Tri-level/Multi-level power supply (TLP/MLP) 210. The TLP/MLP 210 supplies DC high voltage power (e.g., 95V or 140V) to the transducer elements 12 of the probe 14. These high voltages excite the transducer elements 12 to produce the focused beams of ultrasound pulses as described herein. The AC/DC converter 218 may supply DC power (e.g., 24V at 300W) to a 3D PS 212 to operate a motor 204 that controls the positioning of the probe 14.

The AC/DC converter 218 also supplies DC power to a front end PS 214 (e.g., 24V at 300W power supply). The front end PS 214 divides the power received from the converter 218 into multiple voltage level outputs for use by the scanning subsystem 11. For example, the receiver board 48 of the receiver boards group 40 may have the ASICs (e.g., ASIC 61) of the ASIC groups 50, 51, 52, and 53 driven at a certain voltage level. The A/D converter receiver circuits (e.g., A/D converter group 54) of board 48 may be driven at a different voltage level. Different levels of voltage may be supplied to each of the receiver boards 42, 44, 46, and 48 of the receiver boards group 40. Likewise, for the transmitter circuits (e.g., the ASICs and A/D converter circuitry) of the transmit boards group 100, different levels of power may be provided to each of the transmit boards 102, 104, 106, and 108. A run/stop (unfreeze/freeze) selector 202 (e.g., a run/stop button 202) may be provided at the user interface 124 and operated by the user to activate a scan operation. It should be noted that the receiver boards group 40 and transmit boards group 100 may consume a large amount of power and produce a large amount of heat. Fans 224 and 226 may be operated at yet another voltage level to cool the circuit components of the corresponding receiver boards group 40 and the transmit boards group 100.

The AC/DC converter 218 supplies DC power to an all local PS 216 component (e.g., power at 24V at 600W). The local PS 216 provides power to local power supplies that may be located at or near individual boards or components of the system 10. For example, FIG. 2 shows a local PS 206 supplying power to the preamplifier boards group 30 and a local PS 208 supplying power to the RFI board 118.

The power consumed at the components of the scanning subsystem 11 may be controlled or managed depending on a mode of operation of the ultrasound system 10. The mode may be determined in part by a user selecting the run/stop selector 202 to activate or deactivate scanning. When scanning is active, the transmit boards group 100 transmit control signals to the probe 14. The probe 14 generates ultrasound pulses that are emitted into, for example, the patient. Image acquisition circuits (e.g., the probe 14, the transducer interface board 20, the preamplifier boards group 30, and the receiver boards group 40) acquire image data. Image processing circuits at the RFI 118 and/or the BEP 122 process the acquired image data into displayable images for display at the user interface 124 as described herein in any known manner. When scanning is not active, image acquisition circuits, for example, circuits of the transmit boards group 100 and of the receiver boards group 40, may be operated at substantially less or at no power.

Figure 3:
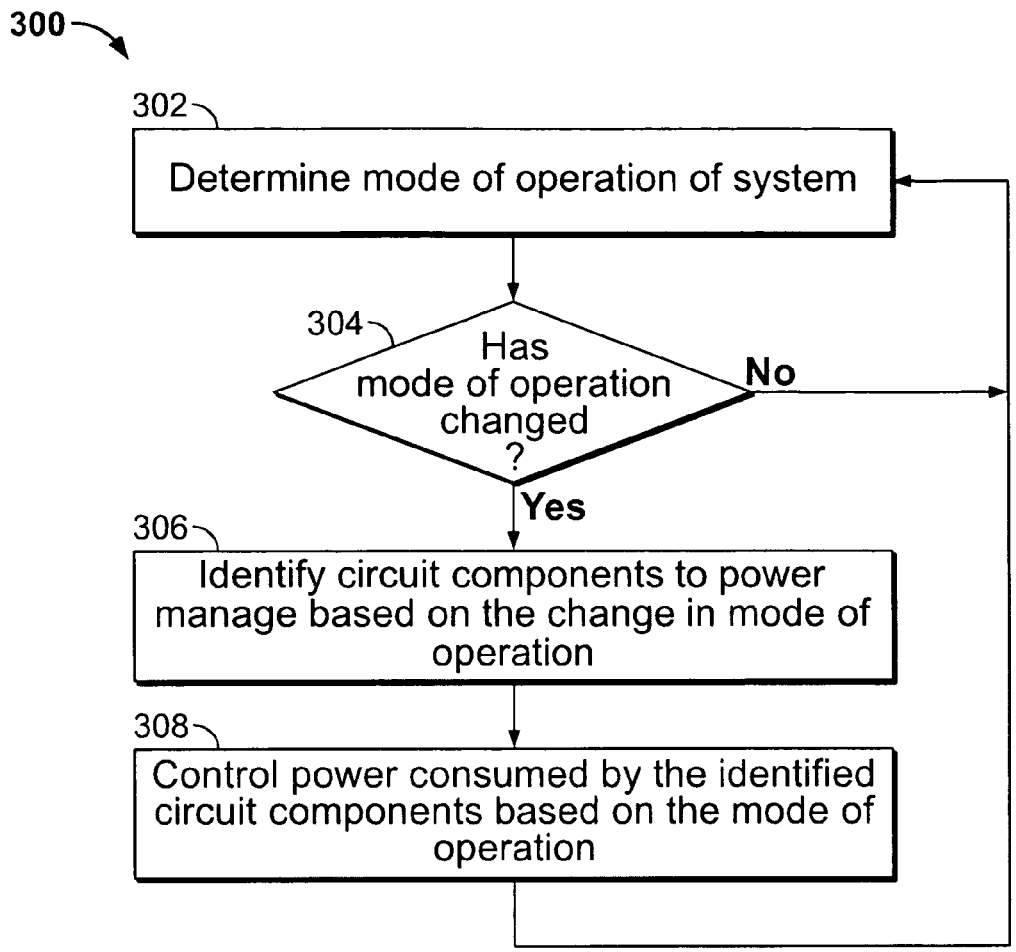
FIG. 3 is a flowchart of a method for controlling power distributed to and consumed by components of the ultrasound system of FIG. 1.

FIG. 3 is a flowchart of an exemplary method 300 for controlling power distributed to and consumed by components of the ultrasound system 10 of FIG. 1. The technical effect of the method 300 is to control consumption of power by the components of the ultrasound system 10. Power control, for example, a power level, in various embodiments may be based on a mode of operation of the ultrasound system 10. For example, when components of the ultrasound system 10 are not in use or are operated with reduced power requirements, power supplied to and consumed by the components may be reduced. Further, and for example, when the system 10 is not actively scanning a patient, the components comprising the scanning subsystem 11, for example, the probe 14, the transducer interface board 20, the preamplifier boards group 30, the receiver boards group 40, the transmit boards group 100, and the RFI board 118, may not need to be powered.

Specifically, and with respect to the method 300, at 302, a mode of operation of the ultrasound system 10 is determined. The mode of operation of the ultrasound system 10 may be determined in part by whether the scanning subsystem 11 is actively acquiring imaging data (e.g., by the state of the run/stop (unfreeze/freeze) selector 202). The mode of operation also may be determined in part by a number of transducer elements 12 (FIG. 1) having been selected for use during the acquisition of imaging data. The number of transducer elements 12 selected for use during a scan operation may also determine the number of circuits (e.g., the A/D converter group 54 and the ASIC 61) to be used in the receiver boards group 40 and the transmit boards group 100 during a scan operation.

The ultrasound system 10 is actively scanning a patient when emitting ultrasound pulses into the patient and collects the reflected ultrasound echoes at the ultrasound probe 14. Signals from the ultrasound probe 14 based on the collected echoes are communicated to the transducer interface board 20, amplified at the preamplifier boards group 30, and then communicated to the receiver boards group 40 to be processed into imaging data using any known method. In this manner, signals from the transducer elements 12 of the probe 14 are processed into acquired imaging data by the image acquisition circuits, for example, the A/D converter group 54 and the ASIC 61 of the scanning subsystem 11. The acquired imaging data may then be communicated to image processing circuits of the RFI board 118 and/or the BEP 122, with the acquired imaging data processed into displayable images for display on the user interface 124.

Power requirements for the components of the ultrasound system 10 may vary. The user or operator of the ultrasound system 10 may not actively be scanning a patient, for example, may be processing reports generated for the patient or may be analyzing images currently displayed at the user interface 124. Further, depending on a type or modality of scan to be performed on a patient, not all of the transducer elements 12 of the probe 14 may be required for the scan. Some scan types or modalities include, for example, A-mode, B-mode, M-mode, 3D imaging, pulse wave Doppler (PWD), and continuous wave Doppler (CWD). For example, a multi-line acquisition (MLA) or 3D imaging may use all of the transducer elements 12. In contrast, a CW Doppler-mode scan may use only half of the transducer elements 12 of the probe 14. When using a lesser number of the transducer elements 12 to perform scanning, a lesser number of transmit circuits on the transmit boards group 100 and/or a lesser number of transmit boards 102-108 may be required. Likewise, when using a lesser number of transducer elements 12, a lesser number of receiver circuits on the receiver boards group 40 and/or a lesser number of receiver boards 42-48 may be required. The mode of operation of the system 10, based in part on whether scanning is active and/or in part on the number of transducer elements 12 used in the scanning, may determine a lesser amount of power to be supplied to the circuit components of the scanning subsystem 11.

At 304, a determination is made as to whether a change in the mode of operation has occurred. If no change in the mode of operation has occurred, processing returns to 302 where again a determination is made as to the mode of operation is made. At 302, processing may wait for a period of time before determining the mode of operation and proceeding to 304. If at 304, a determination is made that the mode of operation has changed, at 306 the circuit components associated with the mode of operation (e.g., circuit components used in that mode of operation) are identified based on the change in the mode of operation.

At 306, the BEP 122 may identify circuit components to which a power level should be adjusted to thereby power manage the components. For example, if the run/stop selector 202 is changed from run to stop, power may not be needed by the probe 14, the transducer interface board 20, the preamplifier boards group 30, the receiver boards group 40, and the transmit boards group 100. In contrast, if the run/stop selector 202 is changed from stop to run, power may need to be supplied to the aforementioned components.

At 308, power consumed by the circuit components identified at 306 is controlled. Various embodiments for controlling the power consumed include, but are not limited to, disconnecting the power supply/source to the component, for example, disconnecting local PS 206 from the preamplifier boards group 30. Alternatively, power may be controlled by controlling digital circuitry that drives the logic levels to power control pins of a circuit component. For example, the logic levels at a set of power control pins on the receiver board 48 may indicate to the receiver board 48 to only supply power to run the fan 224, and further, for example, only when the ambient temperature in the locality of board 48 is above a pre-determined threshold value. Examples of identified circuits and circuit components of the scanning subsystem 11 that may be power managed include amplifier circuits of the preamplifier boards group 30, A/D converter circuits, such as the A/D converter group 54, receiver circuits such as the ASICs and receiver board circuits of the receiver boards 42-48, the ASICs and transmit board circuits of the transmit boards 102-108, the circuits of the RFI board 118, the circuits of the transducer probe 14, motors such as motor 204, and fans such as fans 224 and 226. As described herein, not all transducer elements 12 of probe 14 may be in use for a scanning mode, and thus the probe 14 may be operated at a plurality of power consumption levels depending on the number of transducer elements 12 in use.

The controlling of power at 308 includes increasing the power consumption or decreasing the power consumption, accordingly. For example, if the user has selected via the run/stop selector 202 to begin scanning, powered to and consumed by the circuit components of the scanning subsystem 11 may be increased. In contrast, if the user selects to stop scanning, power to and consumed by the circuit components of the scanning subsystem 11 may be decreased.

Figure 4:
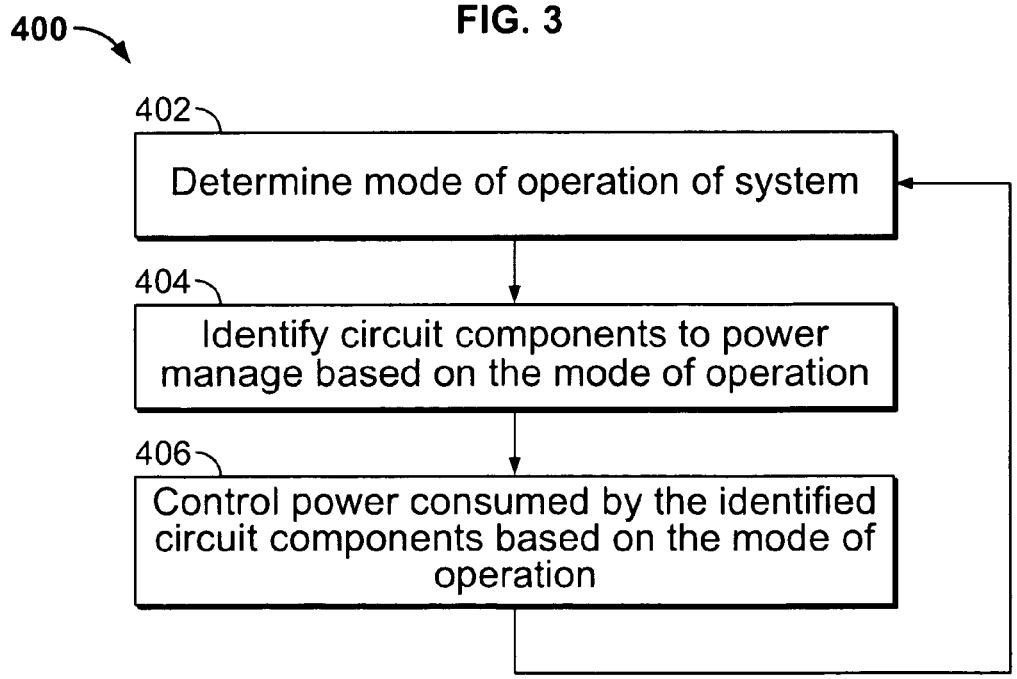
FIG. 4 is a flowchart of another method for controlling power distributed to and consumed by components of the ultrasound system of FIG. 1.

FIG. 4 is a flowchart of another method 400 for controlling power distributed to and consumed by components of the ultrasound system 10 of FIG. 1. Method 400 may periodically control and manage power to the circuit components of the scanning subsystem 11 based on the mode of operation, whether or not a change has occurred in the mode of operation. At predetermined times, the method 400 may check the mode of operation of the system 10, and command the components of the scanning subsystem 11 accordingly. Specifically, at 402, a determination of the mode of operation is made. At 404, circuit components to which a power level is to be controlled to power manage the components, are identified based on the mode of operation. At 406, power consumed by the identified circuit components based on the mode of operation is controlled.

It should be noted that when reference is made herein to increasing or decreasing power, this may include incrementally increasing or decreasing a power level, or turning on or off power.

While the invention has been described in terms of various specific embodiments, those skilled in the art will recognize that the invention can be practiced with modification within the spirit and scope of the claims.

What is claimed is:

1. A medical imaging system comprising:
   a scanning subsystem configured to acquire imaging data and having a plurality of receiver boards and a plurality of transmit boards; and
   a controller configured to selectively control power to at least one of the plurality of receiver boards or the plurality of transmit boards based on a mode of operation of said scanning subsystem determined in part by a number of transducer elements of the scanning subsystem selected to operate during a scan.

2. The medical imaging system of claim 1, wherein the medical imaging system comprises an ultrasound system, said scanning subsystem comprises an ultrasound probe, transmit circuits configured to control ultrasound pulses generated at the ultrasound probe, and receiver circuits configured to receive and process signals from the ultrasound probe.

3. The medical imaging system of claim 1, wherein said controller comprises a backend processor (BEP) configured to selectively control the power to at least one component of said scanning subsystem.

4. The medical imaging system of claim 1, wherein at least one component of said scanning subsystem is controlled to operate at a plurality of power levels.

5. The medical imaging system of claim 1, wherein said scanning subsystem is configured to operate at a reduced power level when said scanning subsystem is not actively acquiring imaging data.

6. The medical imaging system of claim 1, wherein the mode of operation is determined in part by a user input.

7. The medical imaging system of claim 1, further comprising at least one motor configured to move a 3D transducer probe and configured to consume power only during active scanning by said scanning subsystem.

8. The medical imaging system of claim 1, further comprising at least one fan configured to dissipate heat from the medical imaging system.

9. A medical imaging system comprising:
   image acquisition circuits configured to acquire imaging data;
   image processing circuits configured to process the acquired imaging data; and
   a controller configured to selectively control power consumption by at least one of said image acquisition circuits based on a state of one of a run/stop selector and an unfreeze/freeze selector.

10. The medical imaging system of claim 9, wherein said image acquisition circuits comprise an ultrasound probe and receiver circuits, wherein at least one of the ultrasound probe and receiver circuits is further configured to consume a reduced amount of power.

11. The medical imaging system of claim 9, wherein said controller is a backend processor (BEP) configured to selectively control power consumption by at least one of said image acquisition circuits.

12. The medical imaging system of claim 9, wherein an external power source provides power to the system.

13. A method for controlling power of a medical imaging system, comprising:
   determining a mode of operation of the medical imaging system;
   identifying circuit components to control to power based on the mode of operation; and
   controlling a power level supplied to one of a plurality of local power supplies that provide power to the at least one of said identified circuit components based on the mode of operation.

14. The method of claim 13, wherein said determining a mode of operation comprises determining a change in the mode of operation.

15. The method of claim 13, wherein said controlling comprises one of increasing and a power level supplied to at least one of said identified circuit components based upon the mode of operation.

16. The method of claim 13, wherein said controlling comprises controlling a plurality of power consumption levels supplied to at least one of said identified circuit components based upon the mode of operation.

17. The method of claim 13, wherein said controlling comprises controlling digital circuitry to drive logic levels to power control pins of a component.

18. The method of claim 13, wherein said controlling comprises disconnecting a local power source to a component.

19. The method of claim 13, wherein said controlling comprises connecting a local power source to a component.

* * * * *